(12) United States Patent
Larsson et al.

(10) Patent No.: US 6,207,381 B1
(45) Date of Patent: Mar. 27, 2001

(54) METHOD FOR NUCLEIC ACID ANALYSIS

(75) Inventors: Anita Larsson; Björn Persson, both of Uppsala (SE)

(73) Assignee: Biacore AB, Uppsala (SE)

( * ) Notice: Subject to any disclaimer, the term of this patent is extended or adjusted under 35 U.S.C. 154(b) by 0 days.

(21) Appl. No.: 09/165,700

(22) Filed: Oct. 2, 1998

(51) Int. Cl.[7] .................................................. C12Q 1/68
(52) U.S. Cl. ............................ 435/6; 435/810; 435/501; 536/23.1; 536/24.1; 536/24.3; 536/24.31; 536/24.32; 536/24.33; 536/25.3; 935/77; 935/78
(58) Field of Search ..................... 435/6, 810; 436/501; 536/23.1, 24.1, 24.3, 24.31, 24.32, 24.33, 25.3; 935/77, 78

(56) References Cited

U.S. PATENT DOCUMENTS 5,846,729 * 12/1998 Wu et al. .................................. 435/6

FOREIGN PATENT DOCUMENTS

WO 90/06374   6/1990   (WO) .

OTHER PUBLICATIONS

Schwarz et al., "Detection of nucleic acid hybridization using surface plasmon resonance," *Tibtech* 9: 339–340, 1991.

* cited by examiner

*Primary Examiner*—Kenneth R. Horlick
*Assistant Examiner*—Janell E. Taylor
(74) *Attorney, Agent, or Firm*—SEED Intellectual Property Law Group PLLC

(57) ABSTRACT

A method of determining the binding of an oligonucleotide probe to a test nucleic acid sequence comprises the steps of: (a) providing the test nucleic acid sequence in single-stranded form, (b) contacting the test nucleic acid sequence under hybridizing conditions with a solution containing an oligonucleotide probe which is complementary to a defined portion of a standard nucleic acid sequence, (c) immobilizing to a solid support a nucleic acid fragment at least part of which is complementary to said oligonucleotide probe, (d) contacting the solution from step (b) with said solid support, and (e) determining the amount of binding of oligonucleotide probe present in said solution to its complementary nucleic acid fragment on the second solid support, said amount being inversely related to the amount of binding of the oligonucleotide probe to the test nucleic acid sequence.

16 Claims, 2 Drawing Sheets

METHOD FOR NUCLEIC ACID ANALYSIS

CROSS-REFERENCE TO RELATED APPLICATIONS

This application claims priority from co-pending PCT Application Number PCT/SE97/00549, filed Mar. 27, 1997, which claims priority from Swedish Application Serial No. 9601318-0, filed Apr. 4, 1996, as provided for in 35 USC § 120 and 35 USC § 119 (a) through (d), and in accordance with 35 USC § 365.

FIELD OF THE INVENTION

The present invention relates to nucleic acid analysis, and more particularly to the determination of the binding of an oligonucleotide probe to a test nucleic acid sequence, especially for the detection of sequence variations and quantification of products obtained in amplification reactions.

BACKGROUND OF THE INVENTION

Clinical analyses of DNA sequences are typically directed to determining how a gene in a patient sample differs from a prototypical normal sequence. DNA sequencing through the chain termination method developed by Sanger and Coulson (Sanger et al., Proc. Natl. Acad. Sci. USA 1977; 74: 5463–5467), and the chemical degradation method developed by Maxam and Gilbert (Maxam and Gilbert, Proc. Natl. Acad. Sci. USA 1977; 74: 560–564), or using techniques such as Sequencing By Hybridization (SBH) or Sequencing By Synthesis (see e.g. WO 93/21340) all have the potential to identify mutations and in the same process also reveal the consequence of the mutation at the level of protein coding etc.

Another sequencing approach is disclosed in EP-A-223 618 which described the use of an immobilised DNA template, primer and polymerase exposed to a flow containing only one species of deoxynucleotide at a time. A downstream detection system then determines whether deoxynucleotide is incorporated into the copy or not by detecting the difference in deoxynucleotide concentrations entering and leaving the flow cell containing the complex of DNA template and polymerase.

For screening purposes, however, it is often sufficient, at least initially, to identify deviations from the normal sequence but without directly revealing how a sequence differs from the normal one or only roughly locating the mutation. There are a number of such techniques which speed up analysis as compared to those that involve DNA sequence determination.

One such method uses "label-free" detection based on surface plasmon resonance (SPR) for determining the binding of a short oligonucleotide probe to a single-stranded target sequence immobilised to a sensor chip. Since a mismatch significantly affects the binding affinity, the presence of a sequence deviation may be determined. This method has, however, several disadvantages, such as that it requires immobilizing long target sequences, usually PCR products, to the sensor chip and that the sensor chip can not be regenerated.

SUMMARY OF THE INVENTION

The object of the present invention is to provide a method for determining the binding of an oligonucleotide probe to a test sequence, which method is devoid of the above disadvantages and which may be used for mismatch (mutation) detection as well as amplification (such as PCR) product quantification.

In accordance with the present invention, the above and other objects and advantages are achieved by a method of determining the binding of an oligonucleotide probe to a test nucleic acid sequence, comprising the steps of:
a) providing the test nucleic acid sequence in single-stranded form,
b) contacting the test nucleic acid sequence under hybridising conditions with a solution containing an oligonucleotide probe which is complementary to a defined portion of a standard nucleic acid sequence,
c) immobilizing to a first solid support a nucleic acid fragment at least part of which is complementary to said oligonucleotide probe,
d) contacting the solution from step b) with said first solid support, and
e) determining the amount of binding of oligonucleotide probe present in said solution to its complementary nucleic acid fragment on the first solid support, said amount being inversely related to the amount of binding of the oligonucleotide probe to the test nucleic acid sequence.

In a preferred embodiment, the test nucleic acid sequence is immobilized to a second solid support. In this case, the probe-containing solution is preferably separated from this second solid support before being contacted with the immobilized complementary nucleic acid fragment.

This and other preferred embodiments of the invention are described in more detail below.

DETAILED DESCRIPTION OF THE INVENTION

The method of the invention is based on the fact that a mismatch base considerably affects the affinity of a short oligonucleotide to a complementary sequence of a single stranded target sequence. A basic feature of the invention is that the detection is performed on oligonucleotide probe that has not bound to the target or test nucleic acid sequence rather than on probe that has bound thereto. This inhibition type approach offers several advantages. Firstly, the problem of having to bind long PCR products to a sensing surface is eliminated. Secondly, the sensing surface will be regeneratable, since the bound probe can easily be removed from the surface, in contrast to a biotin/avidin-bound PCR product, for example. Thirdly, since the PCR product is not bound to the sensing surface, and in a preferred embodiment bound to another solid phase, high temperature treatment to melt apart secondary structures of single stranded DNA can conveniently be carried out, as will be described further below. Finally, as will also be described in more detail below, the method permits analyses to be performed in a multispot or multichannel format.

The term nucleic acid as used herein is to be interpreted broadly and comprises DNA and RNA, including modified DNA and RNA, as well as other hybridising nucleic acid-like molecules, such as e.g. PNA (peptide nucleic acid). This also applies to the term oligonucleotide probe. The size of the oligonucleotide probe is suitably within the range of, say, from 7 to 24 bases, e.g. from 13 to 17 bases, but longer or shorter probes are also possible.

In one embodiment of the invention, the method is adapted for detecting one or more sequence deviations, such as mutations, and the approximate position thereof in a nucleic acid fragment, usually a DNA fragment. Although the method may be performed with a single oligonucleotide probe for detecting a specific mutation, it is preferred to use at least two, and preferably a number of oligonucleotide probes so that the probes together cover a whole DNA sequence to be tested, such as a PCR-amplified DNA sequence. The probes should then overlap by at least one base, and preferably by two or three bases. Such an analysis may be performed as follows.

Target DNA, usually PCR-amplified DNA from a patient, is bound to a solid phase. The binding to the solid phase may, as is well known in the art, for example, be effected by including one member of a terminal specific binding pair in the PCR product and providing the other member attached to the solid phase. The PCR product may, for example, be biotinylated and the solid phase coated by avidin or streptavidin, such as streptavidin-coated magnetic beads which are commercially available.

The bound DNA is then made single-stranded, for instance by treatment with sodium hydroxide, and incubated with a mixture of short oligonucleotides, e.g. 13–17-mers, which together cover the whole PCR product, or a desired part thereof to be analysed, as mentioned above.

The immobilised single-stranded DNA may form a secondary structure, and to avoid that a part or parts of the DNA sequence will thereby be unavailable for hybridisation with the oligonucleotides, the incubating mixture is preferably heated, for example to 94° C., for a suitable time, such that the secondary structures are melted apart. On cooling, the oligonucleotides present will then compete with, and in most cases dominate the reformation of the secondary structure.

After completing the incubation, i.e. at equilibrium between oligonucleotide probe in solution and oligonucleotide probe bound to the immobilised PCR product, the solution is preferably separated from the solid phase. The concentrations of the respective oligonucleotide probes in the solution are then determined by contacting the solution with immobilised single-stranded DNA sequences, usually oligonucleotides, which are complementary to the oligonucleotide probes, to hybridise the probes to the immobilised DNA, and determining the amount of each probe that has bound to its respective complementary immobilised DNA sequence.

Any deviation of the PCR product tested from the wild-type sequence will result in the corresponding oligonucleotide probe being mismatched in at least one base, and thereby having a lower affinity to the PCR product, which manifests itself as a higher concentration of the oligonucleotide in the solution in comparison with that of the wildtype case. The comparison with the wildtype sequence may be performed by also carrying out the above described test on the wildtype sequence or, alternatively, by relating each concentration obtained to a previously prepared standard curve.

The deviation may be a point mutation, an insertion or a deletion, and the particular probe that deviates from the wildtype case also indicates the location of the deviation.

The above-mentioned complementary sequences to which the residual probes in the solution are hybridised may be immobilised to separate solid phase surfaces or separate areas of a single surface. In the first-mentioned case, the probe-containing solution is contacted with the different surfaces serially (e.g. by passing the solution through a number of flow cells), and in the latter case in parallel (multispot detection).

While it is preferred to immobilize the target DNA to a solid phase, as described above, the analysis procedure may also be performed with the target DNA in solution. Double stranded DNA may then be made single stranded by heating.

Various detection principles may be used for detecting the probes that bind to the immobilised complementary sequences in the final step. For example, the oligonucleotide probes may be labelled by a detectable tag, such as by a chromophore or fluorophore, in which case the amount of label be determined by suitable photometric means as is well known in the art. For example, the complementary sequences may be immobilised in defined positions on a chip and the labels detected by a CCD camera.

Also so-called label-free detection techniques may advantageously be used. Among such techniques are surface sensitive detection methods where a change in a property of a sensing surface is measured as being indicative of binding interaction at the sensing surface. Exemplary are mass detecting methods, such as piezoelectric, optical, thermo-optical and surface acoustic wave (SAW) methods, and electrochemical methods, such as potentiometric, conductometric, amperometric and capacitance methods.

Among optical methods may particularly be mentioned those that detect surface refractive index, such as reflection-optical methods, including both internal and external reflection methods, e.g. ellipsometry and evanescent wave sensing, the latter including surface plasmon resonance (SPR), Brewster angle refractometry, critical angle refractometry, frustrated total reflection (FTR), evanescent wave ellipsometry, scattered total internal reflection (STIR), optical wave guide sensors, evanescent wave based imaging, such as critical angle resolved imaging, Brewster angle resolved imaging, SPR angle resolved imaging, etc., as well as methods based on evanescent fluorescence (TIRF) and phosphorescence. Presently attractive methods are SPR and FTR for which there are commercial instruments.

In the case of mass or refractive index sensing methods, the detected hybridisation response may be amplified by binding a specific "secondary" reagent to the bound oligonucleotide probe, for example an antibody directed to an antigenic tag on the probe.

It is readily understood that the above described method can be used for scanning or screening large numbers of DNA sequences for the presence of mutations. The method is also well suited for identification tests, such as the identification of virus or bacterial strains, HLA typing, etc.

In another embodiment of the present invention, the method is used for quantification of amplified nucleic acid products. To be able to quantitatively determine the amount of nucleic acid amplified by PCR (polymerase chain reaction) or related amplification methods, the sample DNA, the amount of which in the sample is unknown, is amplified together with a known quantity of a "competitor" DNA of similar structure. By determining the relative amounts of amplified target and competitor DNA, the initial amount of target DNA in the sample may be determined which is of importance for many diagnostic applications.

In accordance with the invention, the mixture of amplified target DNA and competitor DNA is immobilised to a solid phase, e.g. to magnetic streptavidin-coated beads in the same way as in the first embodiment described above. After making the DNA single-stranded, the solid phase is then incubated with (i) an oligonucleotide probe complementary to the target DNA and (ii) an oligonucleotide probe complementary to the competitor DNA, and optionally also (iii) an oligonucleotide probe complementary to a common sequence of the target DNA and the competitor DNA. The solution is preferably first separated from the solid phase, and the concentrations of the respective oligonucleotides in the solution are then determined by contacting the solution with immobilised oligonucleotides complementary to the respective probes in the same way as in the first described embodiment. From the concentration values obtained, the amount of amplified target DNA can be determined, and thereby also the amount of initial target DNA in the sample.

The above described method of quantifying nucleic acid products from amplification reactions may, of course, be combined with detection of sequence deviations or mutations, such that a nucleic acid fragment may be tested both qualitatively and quantitatively at the same time.

The invention will now be illustrated by the following non-limiting Examples, reference being made to the accompanying drawing.

EXAMPLES

The analyses were carried out on a BIAcore® 2000 system (Pharmacia Biosensor AB, Uppsala, Sweden) with a Sensor Chip SA (Pharmacia Biosensor AB) as the optical sensor surface. The instrument was provided with an integrated µ-fluidic cartridge (IFC) which allows analysis in four cells by a single sample-injection.

Example 1

Detection of a Sequence Mutation

A model system was set up based on synthetic oligonucleotides.

Magnetic streptavidin-coated beads (Dynabeads™ from Dynal, Norway) were washed according to the manufacturer's instructions.

Two different biotinylated 17-mer oligonucleotides:

normal: biotin-TGA CAG AAA CAC TTT TC mutated: biotin-TGA CAC AAA CAA TTT TC were diluted in buffer of a high ionic strength (50 mM Hepes, 1 M NaCl, pH 7.4) 1:2 in the range 1–0.00195 µg/ml. 80 µl of each dilution was incubated for 15 minutes with 20 µl magnetic beads. Buffer without oligonucleotide was used as control. The oligonucleotide solutions were removed and the magnetic beads were washed twice with the above buffer.

60 µl of a FITC (fluoresceinisothiocyanate) labelled 13-mer oligonucleotide 100% complementary to the normal sequence was added to all tubes, the 13-mer being diluted to the concentration 0.05 µg/ml if the above buffer with addition 1% Tween® 20. Incubation was performed for 15 minutes.

The solutions were removed from the magnetic beads, and the beads were then washed with 20 µl buffer containing the reagent. The two volumes obtained were pooled.

Figure 1:
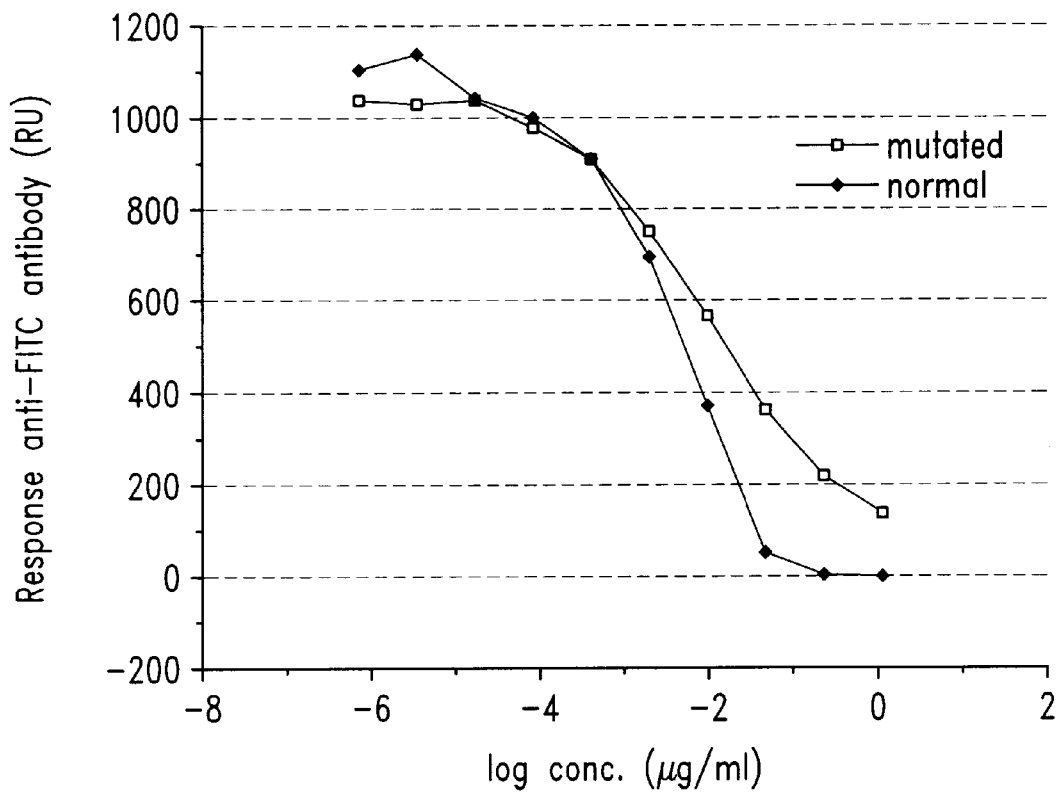
FIG. 1 is a plot of relative response (in RU) in SPR assay of FITC-labelled oligonucleotide remaining in solution after incubation with complementary wildtype target and mutated, respectively, oligonucleotide bound to magnetic beads, versus concentration of complementary oligonucleotide bound to the magnetic beads (in µg/ml).

The normal sequence was immobilised via a streptavidin chip SA in BIAcore® 2000. The test solutions were sequentially injected over the surface with intermediate amplification/increase of the specificity by the injection of a monoclonal antibody directed against FITC and regeneration of the surface with 100 mM NaOH. The results are shown in Table 1 below and in FIG. 1.

TABLE 1

| Oligonucleotide conc. (µg/ml) | Normal sequence Response (RU) | Mutated sequence Response (RU) |
|---|---|---|
| 1 | −7 | 136 |
| 0.5 | −3 | 218 |
| 0.12 | 372 | 563 |
| 0.06 | 700 | 751 |
| 0.03 | 906 | 910 |
| 0.015 | 996 | 976 |
| 0.007 | 1037 | 1031 |
| 0.003 | 1134 | 1027 |
| 0.001 | 1134 | 1037 |

The results demonstrate that the 13-mer oligonucleotide binds less to the mutated sequence which manifests itself as a higher concentration in the solution.

Example 2

Detection of Sequence Deviations

Amplification of p53 gene exon 7 p53 gene templates from four patients (one wildtype and three mutated) were subjected to PCR using the following primers 1 and 2 for amplification of "exon 7" (365 bp) of the p53 gene:

Primer 1: Biotin-TGGCCCCTCCTCCTCAGCATCTTA

Primer 2: Biotin-TGGGCAGTGTCCGCTTAGTG

Each amplification mix consisted of 5 pmol of primers 1 and 2, 20 mM polymerization mix (containing the four nucleotides), 1 unit of Taq polymerase and 5 µl of template diluted in 1× Taq polymerase buffer. The reaction mix was amplified in a thermal cycler (GeneE, Techne) with the following program: step 1—94° C. for 10 minutes; step 2—94° C. for 15 sec, 58° C. for 30 sec, 72° C. for 45 sec; step 3— 72° C. for 7 minutes. Step 2 was repeated 38 times before the procedure was completed by step 3. The product obtained with the wildtype gene is referred to below as "wildtype" while the mutated genes are referred to as "mutation 4", "mutation 6", and "mutation 7", respectively. The wildtype sequence for "exon 7" as well as the positions of the above mutations are shown in the Sequence List at the end of the description.

Detection of Sequence Deviations

Magnetic streptavidin-coated beads (Dynabeads™ from Dynal, Norway) were washed according to the manufacturer's instructions. Two tubes were then incubated with 40 µl of the "wildtype" PCR product obtained above and 40 µl of buffer (50 mM Hepes, 1 M NaCl, pH 7.4). A third tube served as a control and was incubated with buffer. The tubes were treated according to the manufacturer's instructions to make the PCR product single-stranded.

Each tube was then incubated with 60 µl of a mix consisting of thirteen FITC-labelled in 13 bp oligonucleotides, indicated by lines above the respective complementary exon 7 sequence in the Sequence List and designated by the letters D, F, H, J, L, N. P, R, T, V, Y, Å and "7-13", referred to below as "7-d", "7-f", etc and "7-13", respectively. During the incubation, the temperature was changed stepwise: 94° C. for 1 minute, and 55° C., 45° C., 35° C. and 29° C. for 3 minutes each. The solutions were then transferred to respective Eppendorf tubes. Respective oligonucleotides were diluted to 0.05 µg/ml in buffer containing 1% Tween® 20. The magnetic beads were washed with 20 µl buffer which was mixed with the 60 µl already obtained.

Each solution was then analysed in BIAcore™ 2000. Biotinylated 17-mer oligonucleotides "7-d-bio", 7l-bio" and 7p-bio", complementary to oligonucleotides 7-d, 7-l and 7-p above, and a biotinylated oligonucleotide "exon7-bio", biotin-GTT CCT GCA TGG GCG GC, complementary to oligonucleotide 7-13, were immobilised to a respective channel 1 to 4 on the SA sensor chip. Analyses were then performed as described in Example 1 above.

The above described experiment was repeated for the PCR products "mutation 4", "mutation 6", and "mutation 7", respectively. The results are shown in Table 2 below, where responses are expressed in "Resonance Units" (RU).

TABLE 2

|  | 7d-bio Resp. (RU) | 7l-bio Resp. (RU) | 7p-bio Resp. (RU) | Exon7-bio Resp. (RU) |
| --- | --- | --- | --- | --- |
| Blank | 1310 | 3018 | 1956 | 2769 |
| Wildtype | 300 | 1327 | 1201 | 1020 |
| Mutation 4 | 225 | 1216 | 960 | 305 |
| Mutation 6 | 281 | 1161 | 1039 | 1334 |
| Mutation 7 | 691 | 1661 | 1246 | 2254 |

"Wildtype" as well as "mutation 4" are 100% complementary to all oligonucleotides immobilised to the sensor chip. "Mutation 6" has a central mismatch at the end of "exon7-bio", and "mutation 7" has a central mismatch (which lowers the affinity significantly more than an end mismatch).

The expected effect of a point mutation is that a smaller amount of oligonucleotide binds to the PCR product on the solid phase, more oligonucleotide thereby remaining in the solution being analysed. A point mutation thus manifests itself as a higher signal for a certain oligonucleotide than that for the wildtype sequence.

The response for the wildtype sequence on "exon7-bio" amounts to 1020 RU. Mutation 6 (end mismatch) has an increase of about 300 RU, while the response for mutation 7 (central mismatch) is increased by about 1200 RU. The detected increases thus reflect the mutations.

Example 3

PCR Product Quantification

A 97 bp sequence of a plasmid, which harboured a sequence specific for chlamydia (*Chlamydia trachomatis*) was amplified by PCR. In a separate reaction was amplified a competitor sequence harboured by another plasmid. The competitor sequence differed from the first-mentioned sequence in that a centrally located 17 bp chlamydia-specific portion had been replaced by a 17 bp sequence taken from the lac operon. The two PCR-products were then mixed in suitable proportions. (In a real case the target and competitor templates are, of course, co-amplified).

Three different biotinylated oligonucleotides identical to the chlamydia-specific sequence, the competitor sequence and a common sequence, respectively were immobilised to a streptavidin sensor chip SA in respective channels of BIAcore™ 2000.

Magnetic streptavidin-coated beads (Dynabeads™ from Dynal, Norway) were washed according to the manufacturer's instructions and then incubated with PCR products of the following compositions:

| Chlamydia-specific (%) | Competitor (%) |
| --- | --- |
| 100 | 0 |
| 80 | 20 |
| 60 | 40 |
| 40 | 60 |
| 20 | 80 |
| 10 | 90 |
| 5 | 95 |
| 0 | 100 |

The magnetic beads were washed, and the DNA was made single-stranded according to the manufacturer's instructions. The beads were then incubated with a mixture of three different FITC-labelled 17-mer oligonucleotides, each complementary to one of the chlamydia-specific sequence, the competitor and a common sequence, respectively, at a concentration of 25 nM (chlamydia-specific and competitor-specific) or 50 nM (common) for 15 minutes, after which the solution and the magnetic beads were separated.

The solution was then injected into the BIAcore™ 2000 instrument in series over the three measuring surfaces immobilised as described above. The response was amplified by the injection of a monoclonal antibody directed against FITC. The surfaces were regenerated by 50 mM NaOH and the next solution was then injected.

Figure 2:
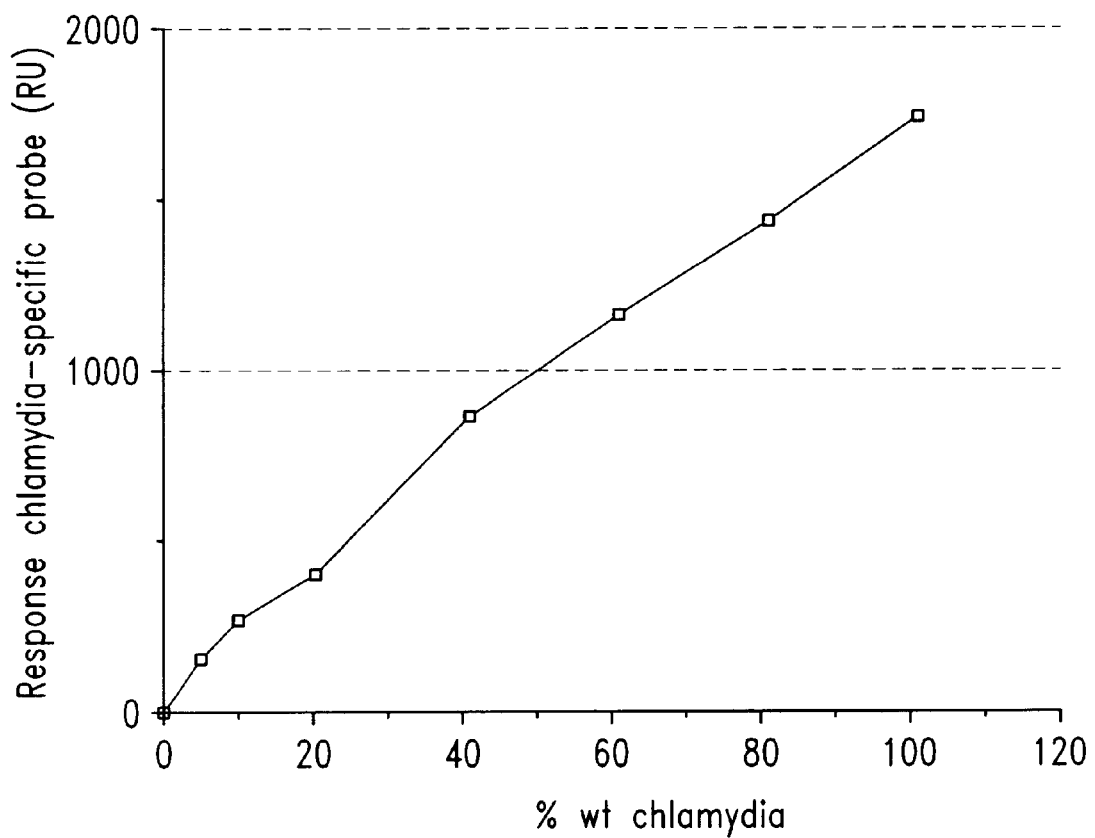
FIG. 2 is a plot of response (in RU) in SPR assay of FITC-labelled chlamydia-specific oligonucleotide remaining in solution after incubation with complementary PCR-amplified chlamydia DNA.

The results are shown in FIG. 2. The figure shows the anti-FITC response for the chlamydia-specific probe after incubation with the different PCR products. The response for the common sequence was used to normalise the specific responses.

What is claimed is:

1. A method of determining the binding of an oligonucleotide probe to a test nucleic acid sequence, comprising the steps of:
   a) providing the test nucleic acid sequence in single-stranded form,
   b) contacting the test nucleic acid sequence under hybridising conditions with a solution containing an oligonucleotide probe which is complementary to a defined portion of a standard nucleic acid sequence,
   c) immobilizing to a first solid support a nucleic acid fragment at least part of which is complementary to said oligonucleotide probe,
   d) contacting the solution from step b) with said first solid support, and
   e) determining the amount of binding of oligonucleotide probe present in said solution to its complementary nucleic acid fragment on the first solid support, said amount being inversely related to the amount of binding of the oligonucleotide probe to the test nucleic acid sequence.

2. The method according to claim 1, wherein said test nucleic acid sequence is immobilized to a second solid support, said solution optionally being separated from the second solid support prior to being contacted with said immobilized nucleic acid fragment.

3. The method according to claim 1, wherein said test nucleic acid sequence may contain a deviation in relation to the standard nucleic acid sequence, and wherein the detected extent of binding of the oligonucleotide probe to the test nucleic acid sequence indicates whether there is a mismatch caused by the presence of a deviation in the complementary part of the test nucleic acid sequence.

4. The method according to claim 1, which further comprises performing steps (a) to (e) also for said standard nucleic acid sequence, and comparing the result obtained for the test nucleic acid sequence with that obtained for the standard nucleic acid sequence.

5. The method according to claim 1, wherein said test nucleic acid sequence is contacted with a solution containing at least two different oligonucleotide probes complementary thereto, and the solution is then contacted with respective immobilized nucleic acid fragments complementary to the respective probes.

6. The method according to claim 5, wherein said probes overlap by at least one two or three bases.

7. The method according to claim 1, wherein the step of contacting said test nucleic acid sequence with the oligonucleotide probe or probes comprises transiently heating to a temperature sufficient to melt apart any secondary structure of the test nucleic acid sequence.

8. The method according to claim 1, wherein said test nucleic acid sequence is a product of an amplification reaction.

9. The method according to claim 8, wherein a competitor nucleic acid sequence, amplified in the same amplification reaction, is provided together with the test nucleic acid sequence and contacted with an additional oligonucleotide probe complementary to the competitor sequence, the amount of the additional oligonucleotide probe in said solution being determined by its binding to an immobilised complementary nucleic acid fragment and compared with the amount of binding of said test nucleic acid sequence-complementary oligonucleotide to the test nucleic acid sequence to thereby determine the original quantitative ratio between test nucleic acid sequence and competitor nucleic acid sequence.

10. The method according to claim 9, wherein said test and competitor nucleic acid sequences are immobilized to said second solid support.

11. The method according to claim 1, wherein the binding of said oligonucleotide probe or probes to said immobilized complementary nucleic acid fragments is determined via detectable labels of said probes.

12. The method according to claim 1, wherein the binding of said oligonucleotide probe or probes to said immobilized complementary nucleic acid fragments is determine by a surface sensitive detection technique.

13. The method according to claim 12, wherein said first solid support surface or surfaces are optical sensor surfaces.

14. The method according to claim 13, wherein said optical sensor surface or surfaces are part of a detector based upon evanescent wave sensing.

15. The method according to claim 14, wherein said evanescent wave sensing is based on surface plasmon resonance (SPR).

16. The method according to claim 11, wherein said detectable labels are a fluorophore or a chromophore label.

* * * * *